United States Patent
Kruip et al.

(10) Patent No.: US 7,960,710 B2
(45) Date of Patent: Jun. 14, 2011

(54) PARTICLE RADIATION THERAPY EQUIPMENT

(75) Inventors: Marcel Jan Marie Kruip, Oxford (GB); Paul Beasley, Abingdon (GB)

(73) Assignee: Siemens Plc, Frimley, Camberley (GB)

( * ) Notice: Subject to any disclaimer, the term of this patent is extended or adjusted under 35 U.S.C. 154(b) by 760 days.

(21) Appl. No.: 11/917,940

(22) PCT Filed: Jun. 16, 2006

(86) PCT No.: PCT/GB2006/050160
§ 371 (c)(1),
(2), (4) Date: Dec. 18, 2007

(87) PCT Pub. No.: WO2006/136865
PCT Pub. Date: Dec. 28, 2006

(65) Prior Publication Data
US 2010/0013418 A1 Jan. 21, 2010

(30) Foreign Application Priority Data

Jun. 22, 2005 (GB) .................................. 0512716.2

(51) Int. Cl.
*A61B 5/05* (2006.01)
(52) U.S. Cl. ............................... 250/492.3; 250/396 ML
(58) Field of Classification Search ............... 250/492.3, 250/396 ML, 398; 335/296, 299, 216; 324/318–322; 600/407, 410, 423, 424
See application file for complete search history.

(56) References Cited

U.S. PATENT DOCUMENTS

| 6,198,957 | B1 | 3/2001 | Green | |
|---|---|---|---|---|
| 6,725,078 | B2 * | 4/2004 | Bucholz et al. | 600/410 |
| 6,950,001 | B2 | 9/2005 | Kruip | |
| 7,483,732 | B2 * | 1/2009 | Zhong et al. | 600/423 |
| 2004/0199068 | A1 | 10/2004 | Bucholz et al. | |
| 2009/0234219 | A1 * | 9/2009 | Kruip | 600/411 |

FOREIGN PATENT DOCUMENTS

| CN | 1489700 A | 4/2004 |
|---|---|---|
| GB | 2 393 373 A | 3/2004 |
| JP | 2004-527282 T | 9/2004 |
| WO | WO 96/00520 A1 | 1/1996 |
| WO | WO 02/065149 A1 | 8/2002 |

OTHER PUBLICATIONS

English translation of Chinese Office Action dated Sep. 4, 2009 (Ten (10) pages).

(Continued)

*Primary Examiner* — Kiet T Nguyen
(74) *Attorney, Agent, or Firm* — Crowell & Moring LLP (57) ABSTRACT

Particle radiation therapy equipment arranged to apply a charged particle beam in a predetermined direction to a region of application within an imaging volume, comprising a charged particle beam source arranged to direct a charged particle beam in the predetermined direction, further comprising magnetic field generation means for generating a magnetic field in the region of application at the same time that the charged particle beam is applied, wherein the magnetic field generation means is arranged to provide access to the region of application for the charged particle beam, and to provide a homogeneous magnetic field in the region of application of the charged particle beam, said magnetic field being directed substantially in the predetermined direction.

9 Claims, 11 Drawing Sheets

OTHER PUBLICATIONS

B.W. Raaymakers, et. al., *Integrating a MRI scanner with a 6 MV radiotherapy accelerator: dose deposition in a transverse magnetic field*, Physics in Medicine and Biology, Taylor and Francis Ltd., London, GB, vol. 49, No. 17, Aug. 20, 2004, pp. 4109-4118, XP-020023871.

International Search Report dated Oct. 4, 2006 (Thirteen (13) pages).
GB Search Report dated Sep. 27, 2005 (Six (6) pages).

English translation of Japanese Office Action dated Nov. 30, 2010 (four-4-pages).

* cited by examiner

PARTICLE RADIATION THERAPY EQUIPMENT

CROSS-REFERENCE TO RELATED APPLICATIONS

This application is related to co-pending U.S. patent application Ser. No. 11/917,959 filed concurrently herewith.

FIELD OF THE INVENTION

The present invention describes particle radiation therapy equipment which includes a magnet, thereby enabling magnetic resonance imaging (MRI) during particle radiation therapy.

BACKGROUND OF THE INVENTION

Radiation therapy with protons and carbon ion beams has been shown to be effective. In addition it has been shown to result in less damage to tissue than conventional gamma radiation therapy.

However, radiation planning for determining the magnitude and position of a dose to be administered is based on MRI imaging or CT imaging, which may have taken place at a considerable time period before the therapy takes place. In the intervening period, the position of the tissue to be irradiated may have moved, or changed shape. This may result in the irradiation of healthy tissue and or missing diseased tissue, which may lead to a remission.

Figure 13:
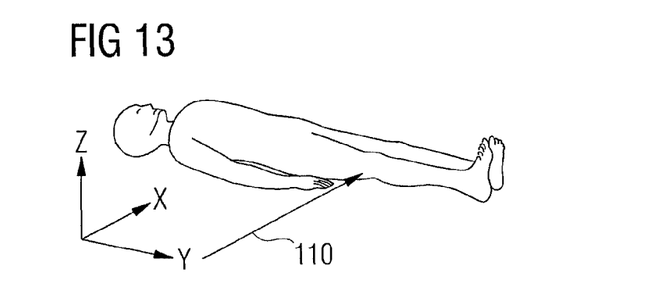
FIG. 13 shows an intended direction of application of a particle beam to a patient for performing particle radiation therapy.

In radiation therapy, the patient is in general irradiated with a beam offered in a transverse direction 110 in transversal plane XY, as schematically illustrated in FIG. 13.

It is desirable for the beam of charged particles to be applied to a patient at the same time as MRI imaging is taking place, since the position and shape of the intended target may then be accurately known in its current position.

The majority of present MRI scanners are not suitable for this because the beam would be obstructed by the cryostat. In addition, even in 'open' scanners such as those employing C- or H- shaped magnets, the magnetic field of the scanner will be perpendicular to the transverse direction 110 of the charged particle beam. This will deflect the beam from the intended direction.

Figure 14A:
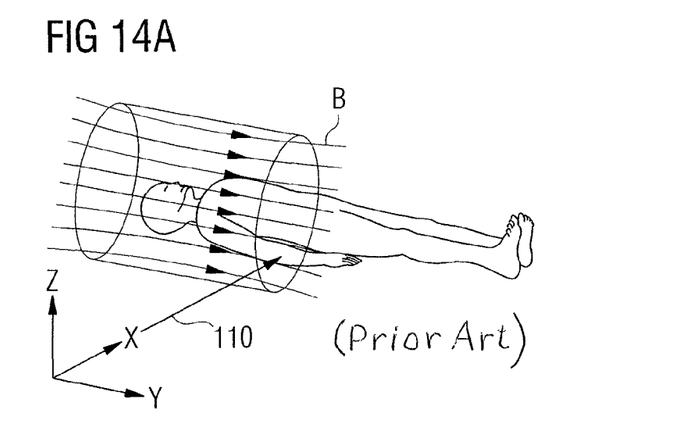
FIGS. 14A and 14B show magnetic fields generated by illustrated conventional MRI magnets with an intended direction of application of a particle beam to a patient for performing particle radiation therapy.
Figure 14B:
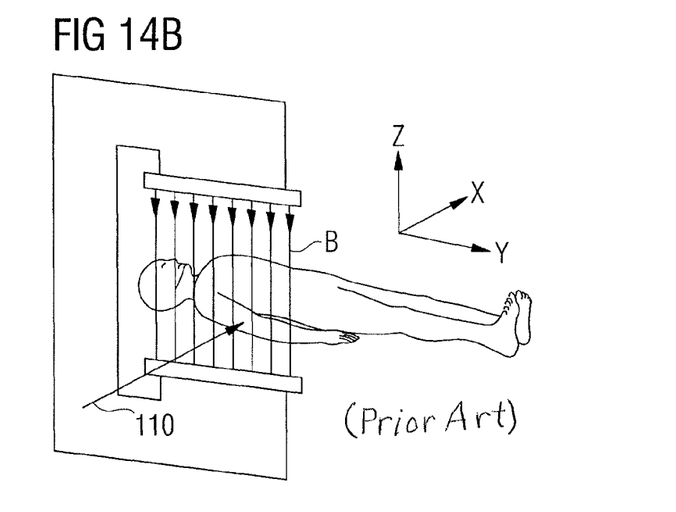

FIGS. 14A and 14B illustrate two prior art MRI scanners, with the magnetic field B illustrated in terms of lines of magnetic flux. FIG. 14A shows a patient undergoing MRI imaging in a conventional solenoidal magnet arrangement. As illustrated, if it were possible to apply a beam of charged particles to the patient in the transverse direction 110 during MRI imaging, the beam would be perpendicular to the magnetic field B produced by the MRI equipment, and so the beam would be deflected from its intended target by the magnetic field B. In such a conventional solenoidal magnet arrangement, it is not possible to access the patient due to the presence of the solenoid surrounding the region of interest of the patient. FIG. 14B shows a patient undergoing MRI imaging in a conventional open C-shaped magnet arrangement. The patient is more accessible in such a magnet arrangement. However, as illustrated, if it were possible to apply a beam of charged particles to the patient in the transverse direction 110 during MRI imaging, the beam would be perpendicular to the magnetic field B produced by the MRI equipment, and so the beam would be deflected from its intended target by the magnetic field B.

US 2004/0199068 describes a system where MRI (magnetic resonance imaging) is used to track the position of a target volume of a patient, and to gate the provision of a particle beam to a treatment volume, so that the particle beam is activated only when the treatment volume coincides with the target volume of the patient.

U.S. Pat. No. 6,198,957 describes a combined MRI and particle beam treatment apparatus. The magnetic field of the MRI system is turned off while the particle beam treatment is applied.

WO 02/065149 describes coil arrangements suitable for use in, for example, MRI apparatus, wherein a magnetic field is produced which is in a direction parallel to the planes of the coils, and to a plane lying intermediate between planes of the coils. It provides a magnet assembly comprising a group of four sets of magnetic coils, each comprising windings of electrically conductive material; wherein the sets of magnetic coils are arranged symmetrically about an axis of intersection of a midplane and a plane of reflection, the plane of reflection being perpendicular to the midplane, such that the coils have a plane of symmetry with respect to another plane, which is perpendicular to both the midplane and the plane of reflection, each of the coils being wound around an axis which is perpendicular to the midplane, and wherein the windings are configured such that, in operation, current flow is symmetrical about the plane of reflection and anti-symmetrical about the midplane, to produce a resultant field at the centre of the system which is perpendicular to the plane of reflection.

According to the present invention, MRI imaging at the same time as particle radiation therapy is enabled by providing an MRI system which operates with a magnetic field in a transverse direction 110 parallel to the intended direction of application of the beam of charged particles, minimising the interference of the magnetic field with the charged particle beam while allowing access to the patient.

The present invention also provides methods for operating such equipment to apply particle radiation to a region of application at the same time as MRI imaging of the same region.

The present invention accordingly provides apparatus and methods as set out in the appended claims.

BRIEF DESCRIPTION OF THE FIGURES

For a better understanding of the invention and to show how the same may be carried into effect, there will now be described by way of examples only, specific embodiments, methods and processes according to the present invention with reference to the accompanying Figures, as shown in the accompanying drawing sheets, wherein.

DETAILED DESCRIPTION OF INVENTION

The present invention provides an application of the magnet coil arrangement described in WO 02/065149 as a means of monitoring the target area for radiation therapy during application of a charged particle beam.

Advantageously, and according to the present invention, such coil arrangements are arranged such that the magnetic field they produce lies in the intended direction 110 of application of a particle beam 102 for particle radiation therapy. Since application of the beam of charged particles will be in the direction of the magnetic field, the beam will not be deflected, and a dose of particle radiation may be accurately applied to the intended target.

Examples of such arrangements will now be described with reference to FIGS. 1-12.

Figure 1:
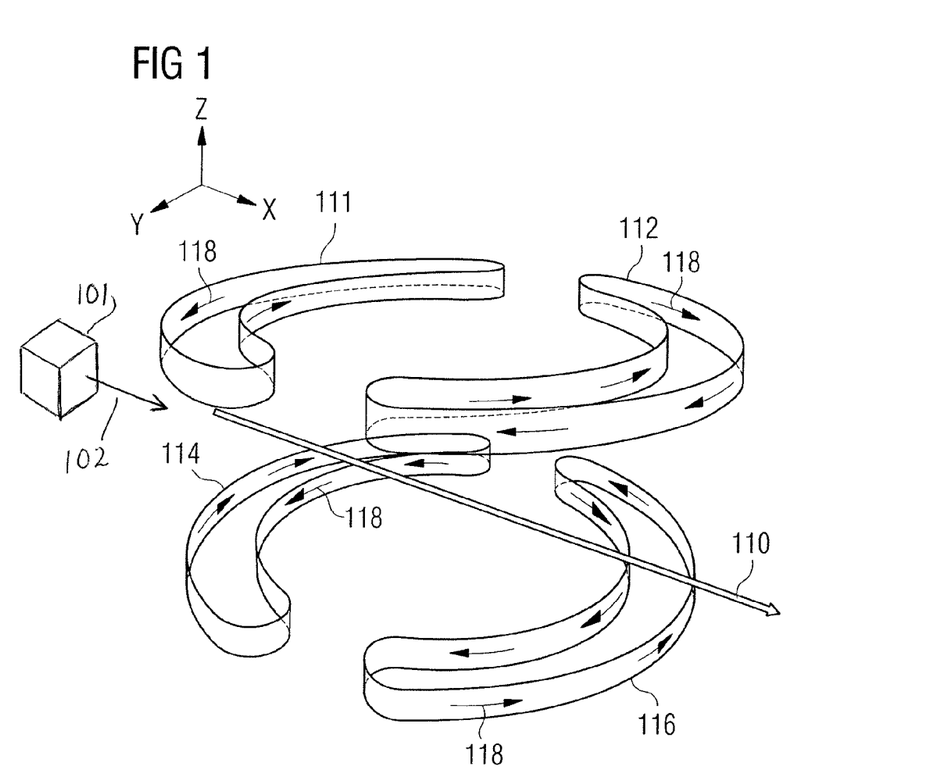
FIG. 1 shows a perspective view of an arrangement of four magnet coils in accordance with an embodiment of the invention.

FIG. 1 shows an arrangement consisting of four coils 111, 112, 114, 116 and a XYZ co-ordinate reference frame, which will be referred to in the following description. The coils 111-116 shown in FIG. 1 are symmetrically arranged with respect to a midplane, parallel to the XY plane, which is also identified as the transverse plane, and also to the YZ plane which is identified as the plane of reflection. The coils also have a plane of symmetry parallel to the ZX plane. The arrows 118 on the coils are shown to demonstrate the direction of the currents in the coils with respect to each other. The direction of currents in the coil 111, which lies above the midplane (XY plane), are opposite (antisymmetrical) to the direction of currents of the coil 114, which lies below the midplane XY. Further, the sense of rotation of the currents of the coils 112, 116 in the positive X space is opposite (in reflective symmetry) to the sense of the currents of the respective corresponding coils 111, 114 in the negative X space. The shape of each coil shown in FIG. 1, sometimes referred to as a 'banana coil' is not straightforward to manufacture by a conventional winding process because of the reversed radius of curvature (concave surface) on the side of the coil closest to the plane of reflection.

The direction 110 of the field produced by the coils 111, 112, 114, 116 and of application of a charged particle beam for particle radiation therapy is indicated by a thick arrow, which will feature in subsequent drawings.

The field generated by a set of coils as shown in FIG. 1 may not produce a field with a quality sufficient for MRI imaging. The following description provides further embodiments which may produce a magnetic field of improved quality.

Figure 2:
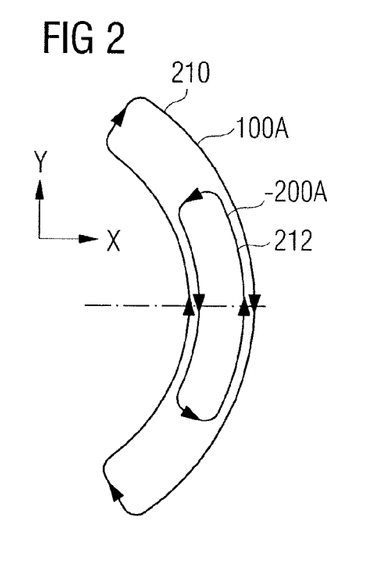
FIGS. 2 and 3 show a comparison of two banana coil configurations.
Figure 3:
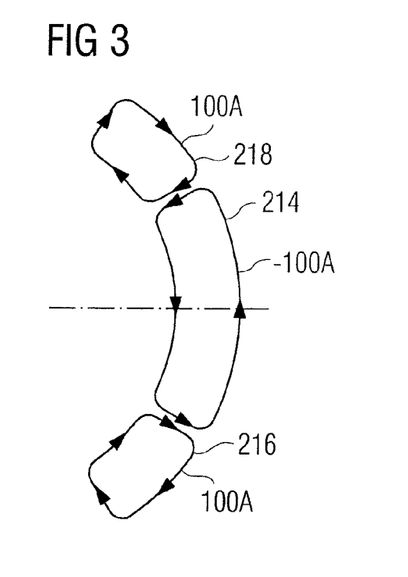

FIGS. 2 and 3 show two further configurations of banana coils suitable for use on in an embodiment of the present invention in an arrangement corresponding to that shown in FIG. 1. The magnetic field produced by each of the configurations of FIGS. 2-3 is the same as for the arrangement of FIG. 1. FIG. 2 shows a nested banana coil wherein a 120° arc banana coil 210 carrying a current of 100 A in a first direction has a 60° arc banana coil 212 nested within. The 60° coil carries a current of 200 A in a direction opposite to the first direction resulting in an overall current of 100 A in the second direction for the centre 60° arc of the whole 120° arc configuration. This is equivalent to the structure shown in FIG. 3 wherein there is a central 60° arc banana coil 214 carrying 100 A current in the second direction with two peripheral 30° arc banana coils 216, 218 carrying 100 A current in the first direction.

Figure 4:
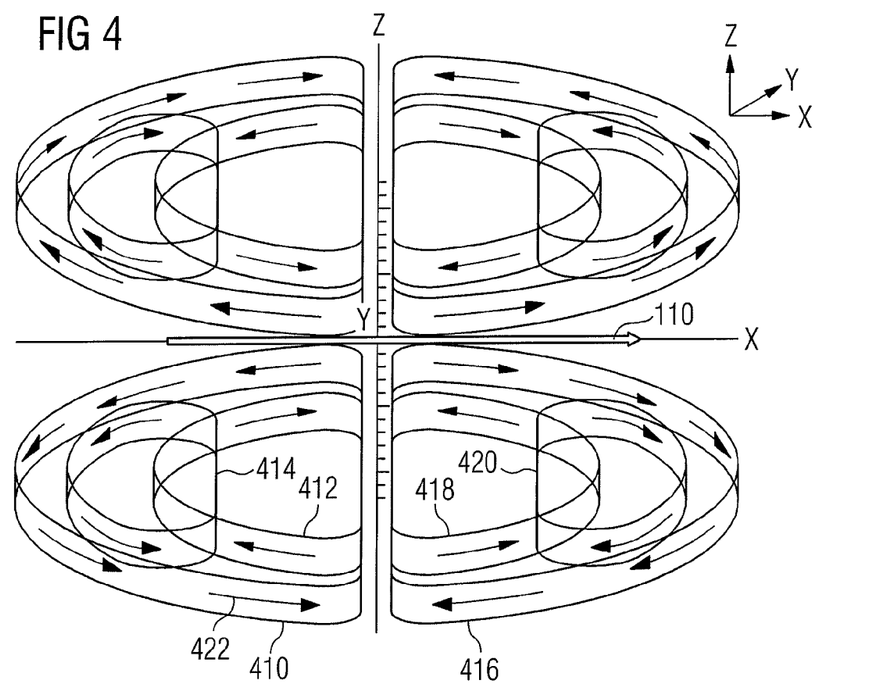
FIG. 4 shows a perspective view of an arrangement of four magnet coil assemblies in accordance with another embodiment of the invention.

Although methods of manufacture for such banana coils are well known, it may be easier to produce substantially the same magnetic field by superimposing D-shaped coils as shown in FIG. 4. This also gives an additional degree of freedom in positioning the straight sides of the D's so as to improve the homogeneity of the field. The D shaped coils can be interleaved and/or over lapping. The coils are arranged with symmetry as discussed with reference to FIG. 1. Referring to the lower coils, it can be seen that coils 410, 412 and 414 have mirror image coils in 416, 418, 420 both in shape and respective current directions, since FIG. 4 also shows the directions of the currents 422 in each of the D-shaped coils.

Each D-shaped coil is wound around an axis which is aligned parallel to the Z-axis in operation. Although the coil is non-circular, the winding is straightforward since there is no reversal in the radius of curvature of the winding. The outer surfaces of each coil are convex, or planar. Whilst a D-shape coil is conventionally expected to have a straight section on one side, in practice, the side need not be completely straight but may merely have an extremely large radius of curvature, to assist in the winding of the wire. For similar reasons, the corners at the ends of the straight section are preferably rounded, rather than comprise a sharp corner. In this way a generally D-shaped coil can be readily wound using a conventional wire winding process but with a variable radius of curvature rather than the fixed radius used for circular coils. Although the axis of winding of each of the individual coils is parallel to the Z axis, the arrangement of the currents in the different coils produces a resultant field at the centre of the system in direction 110 which is perpendicular to the Z axis. Similarly, in the region external to the system the fields of the individual coils serve to cancel each other out, resulting in a very low stray field external to the system without the need for additional shielding measures such as extra coils.

Figure 5:
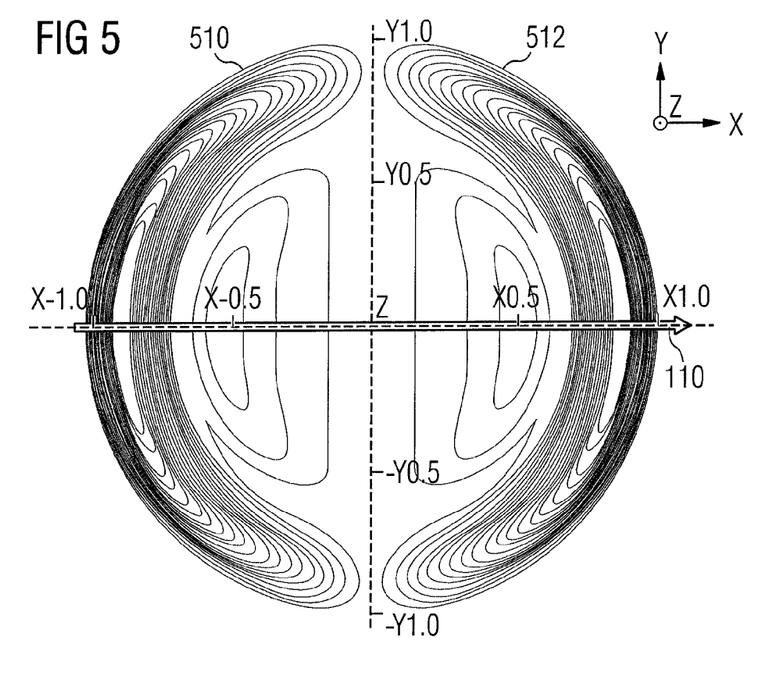
FIG. 5 shows a sectional view of an arrangement in accordance with a further embodiment of the invention.

FIG. 5 shows the top view of a set of planar coils which, theoretically, should produce a high quality homogenous field in direction 110. When arranged in sets with symmetry as discussed with reference to FIG. 1, they will produce a homogeneity which has a predicted peak-peak value of 6 ppm on an imaging region sphere of 40 cm. Coils 510 and 512 are identical, and should be used with current directions (not shown) being mirror images in the YZ plane. These coils are similar in construction to plane or gradient coils, as are known. In contrast to gradient coils, which are configured to provide zero field at the centre of a complete MRI system, in the present application the coils of each quadrant are connected in series so as to provide a high strength, high quality homogeneous field at the centre of an MRI system. However, while this arrangement provides a high strength, high quality homogenous field, it does not allow the accommodation of gradient coils and RF coils, which are required for the generation of an MRI image.

Figure 6:
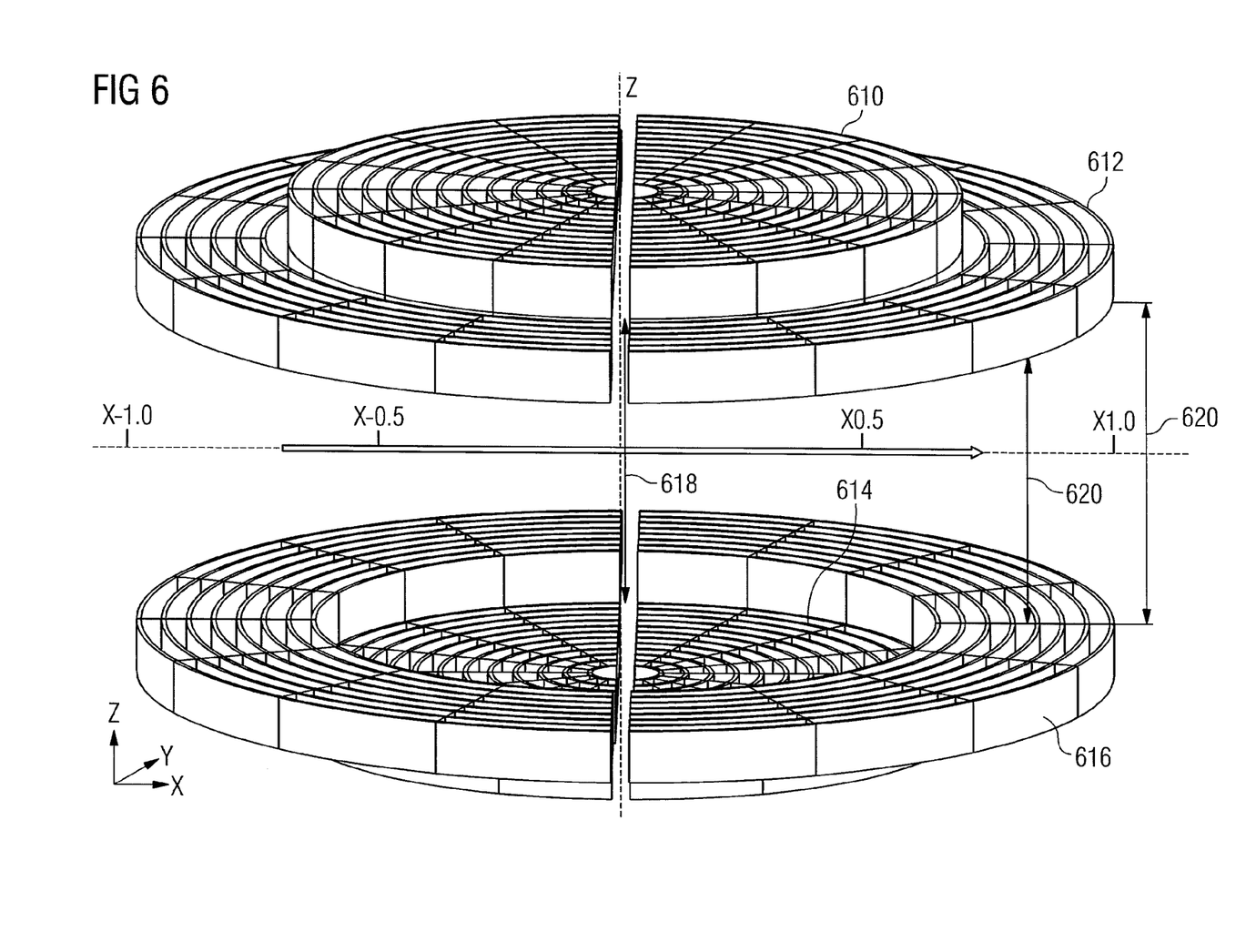
FIG. 6 shows a perspective view of a set of sector shaped coils, with a recess, according to another embodiment of the present invention.

FIG. 6 shows a view of an arrangement of sector-shaped coils 610, 612, 614, 616 in a polar grid fashion. The sector shaped coils are arranged in parallel planes, with a gap 618 between the coils increased for coils in a circle from the centre up to a radius which corresponds to the radius of a gradient coil, manufactured to a current state of art. The central, increased, gap 618 between the central coils 610, 614 provides sufficient space for RF coils, a gradient coil and shims, whilst the gap 620 between the outer coils 612, 616 is less. This improves the homogeneity of the overall resultant field and reduces the amount of conductor required to generate a given central field. The coils may be multiple small segment shaped coils as illustrated. Alternatively, several adjacent segments may be replaced by larger banana coils. In another embodiment, the segment shaped coils may be replaced with trapezium shaped coils, for ease of winding.

Figure 7:
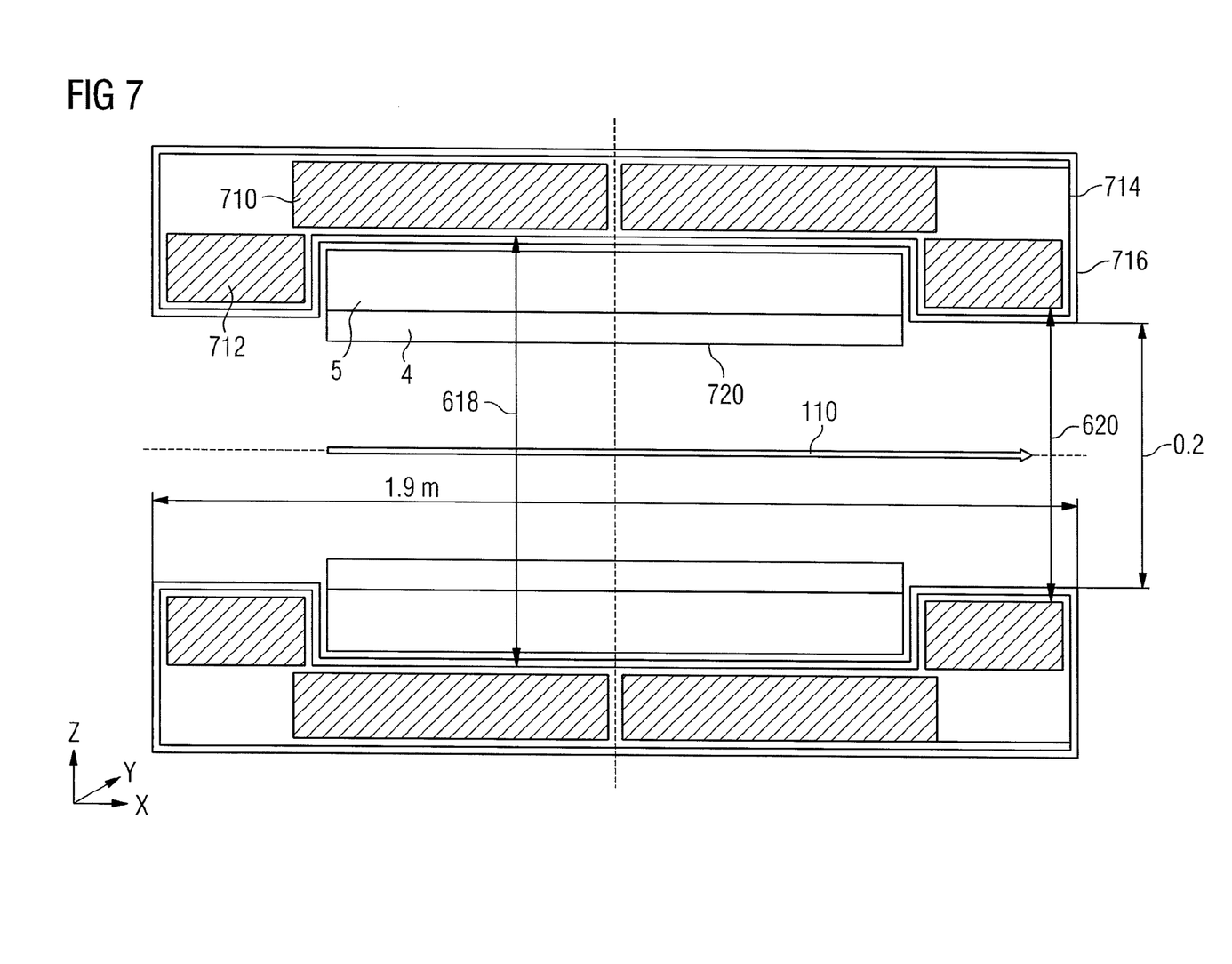
FIG. 7 shows a cross section in the XZ plane, of one embodiment of the invention showing an arrangement of coils such as illustrated in FIG. 6 with respect to other components of an MRI system.

FIG. 7 shows a cross section in the ZX plane of an MRI scanner with an arrangement of coils similar to that shown in FIG. 6. The coils are arranged in two groups, 710 and 712. Group 710 corresponds to the coils 610, 614 with the increased gap 618 in FIG. 6. The coils may be arranged to operate in a superconducting fashion, as is known. The outer coils are identified as 712 corresponding to coils 612, 616 of FIG. 6. Present superconductors require operation at a low temperature and the coils in this example are surrounded by an enclosure, 714, which acts as thermal radiation shield. In addition, this enclosure can also be used to contain a cryogen. The coils 710 and 712 and the enclosure, 714, are surrounded by an airtight enclosure 716.

The inside of this enclosure is evacuated, to minimise the conduction of heat from the inside surface of enclosure 716 to the coils through convection. The enclosure has a recessed part which accommodates a gradient coil assembly 5, and an RF coil 4. The central field has been calculated to be 1 T for a 35 mega-amp-metre coil set, with homogeneity of 143 ppm over a 40 cm diameter sphere. The outside diameter of the conductors is 1.9 m, with a gap 620 between conductors of 0.7 m, and a gap 618 between inner conductors of 0.9 m.

Figure 8:
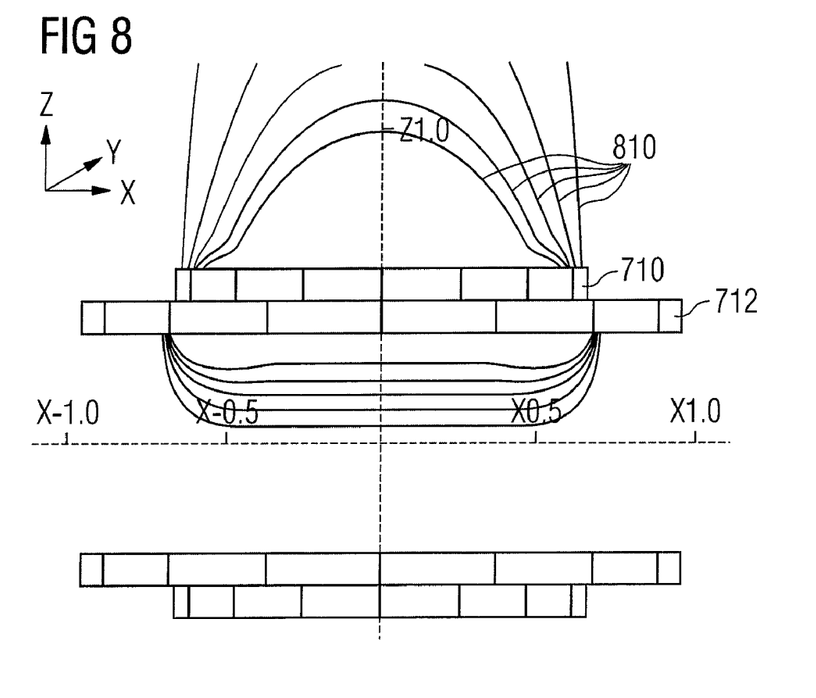
FIG. 8 shows the direction of the magnetic field in the XZ plane for the arrangement of coils shown in FIG. 7 in terms of lines of magnetic flux.
Figure 8A:
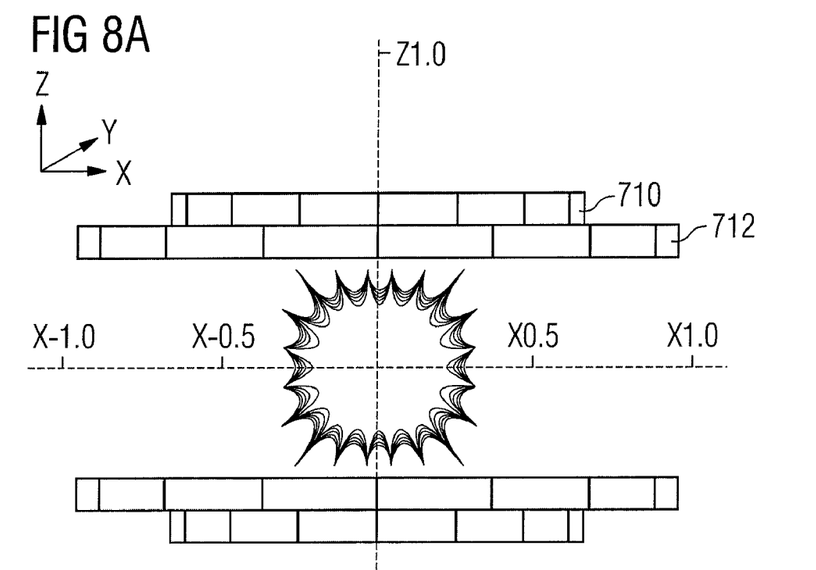
FIGS. 8a to 8c show field intensity contour lines for a magnetic field produced by an arrangement of coils as shown in FIG. 7.
Figure 8B:
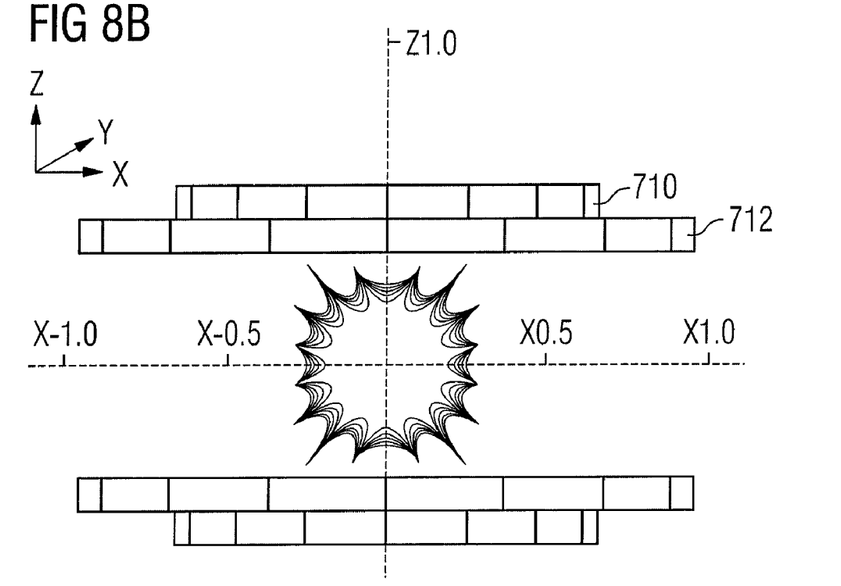
Figure 8C:
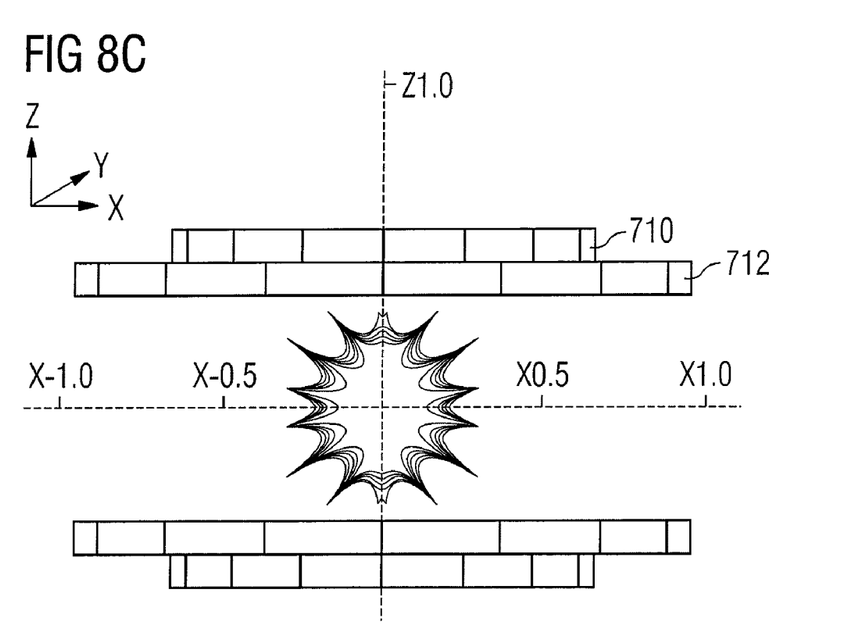

FIG. 8 shows lines of flux 810 in the XZ plane for the embodiment depicted in FIG. 7. The lines show the highly desirable homogenous parallel field produced by the coils, as required for example for magnetic resonance imaging purposes. FIGS. 8a to 8c show, respectively, lines of constant magnetic field strength describing the magnetic field B in the XZ planes at Y=0, Y=0.1 m and Y=0.2 m. The described coil arrangement therefore conveniently provides an embodiment which enables a 0.2 m radius diagnostic volume of sufficient homogeneity to be achieved.

Figure 9:
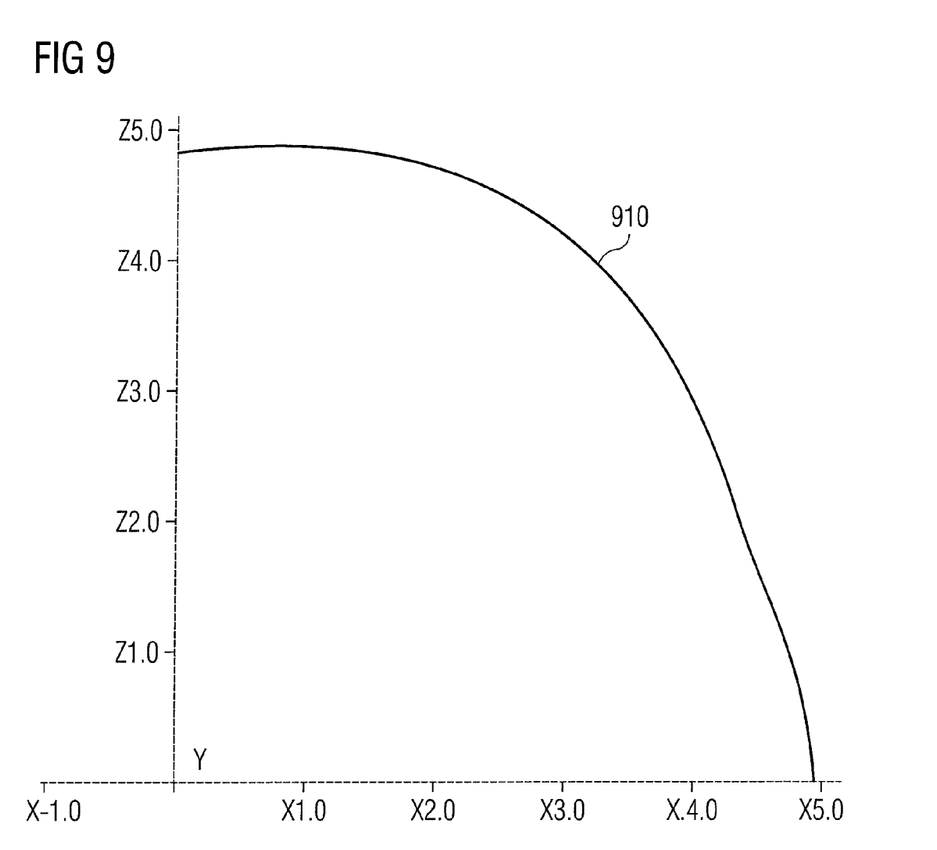
FIG. 9 shows the 5 Gauss line in the XZ plane of the system according to FIG. 7.

FIG. 9 shows the 5 Gauss plot line 910 computed for the coil assembly as described in FIG. 7, in the ZX plane. Only the 5 Gauss line in the +X +Z quadrant is shown. This clearly demonstrates the low stray field characteristics of the described coil arrangement.

Figure 10:
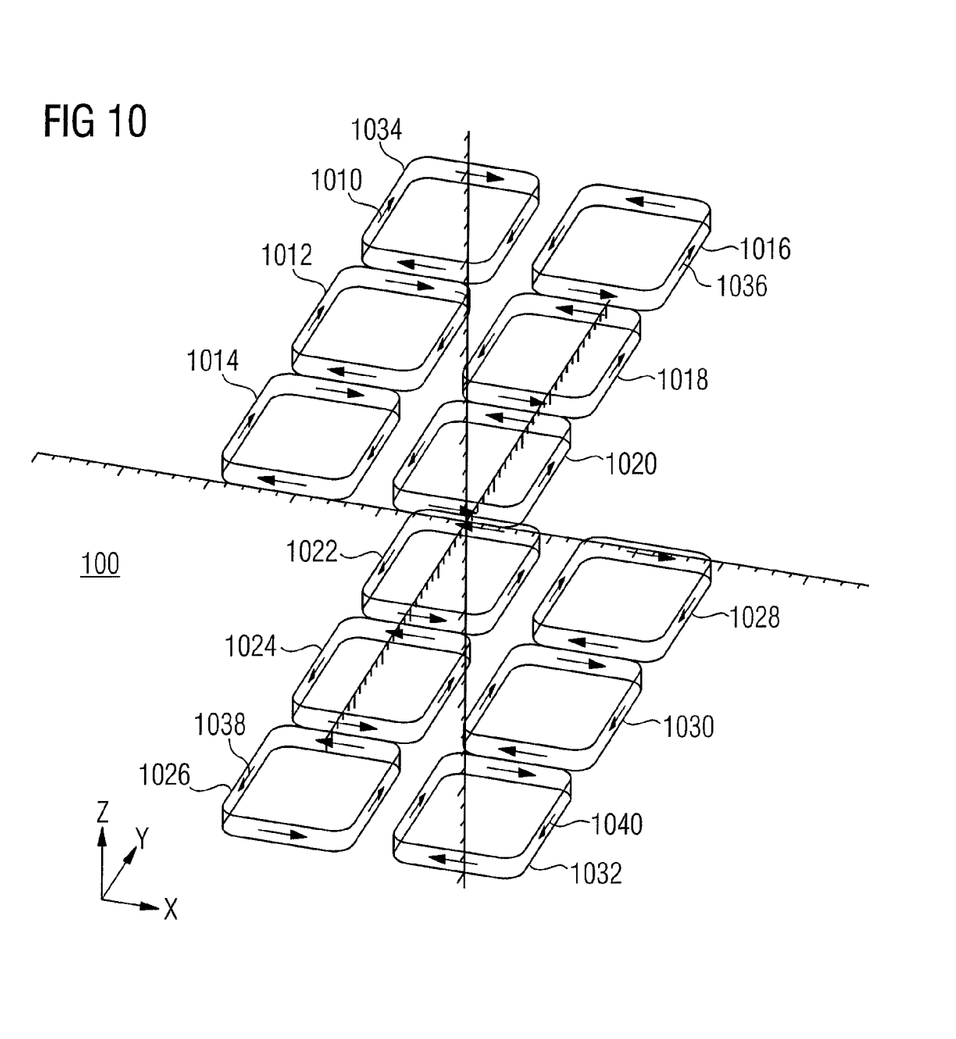
FIGS. 10, 11 and 12 show alternative embodiments.

FIG. 10 shows, in perspective view, all the primary magnets of one embodiment 1000. Each quadrant comprises three coils 1010, 1012, 1014 ... 1032, in side-by-side relationship, with the central coils 1012, 1018, 1024, and 1030 lying in the XZ plane. The current flow directions 1034-1040 in each coil of a quadrant are the same.

Figure 11:
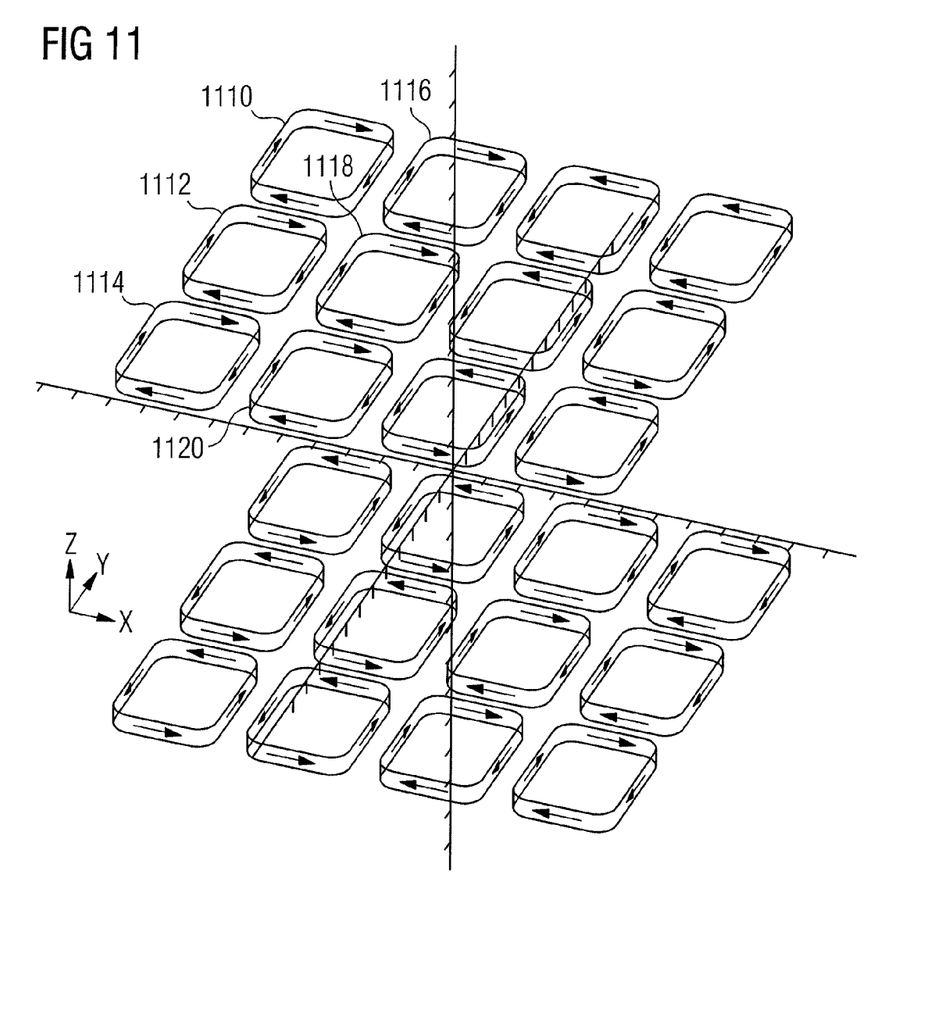

FIG. 11 shows a similar arrangement to FIG. 10, except that there are six coils 1110-1120 in each quadrant. It will be appreciated that it may be desirable to have a broad imaging area for certain applications. Alternatively, the use of a number of small, sub-coils may enable manufacturing costs to be reduced.

Figure 12:
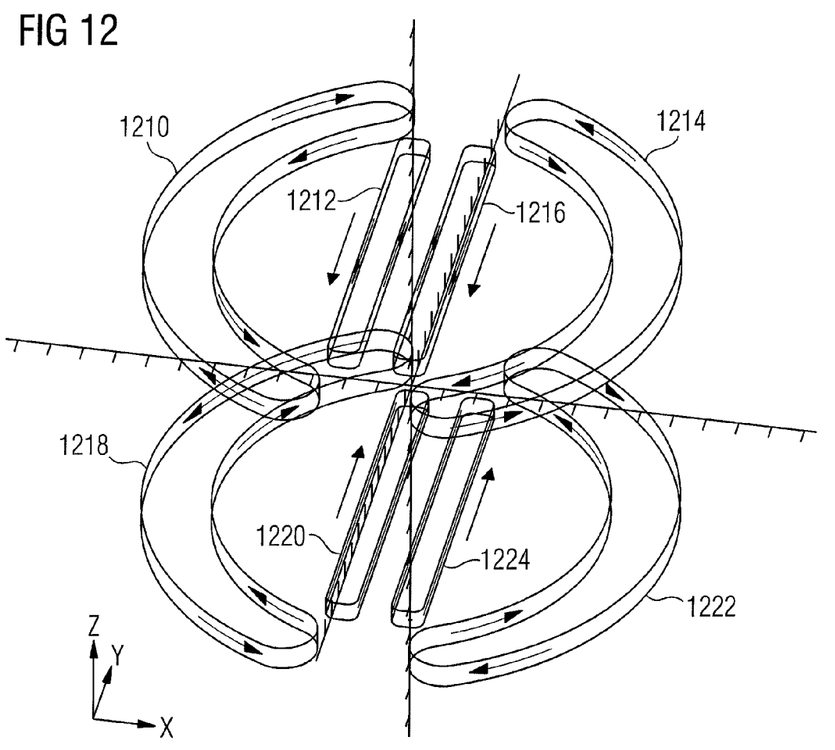

FIG. 12 corresponds with FIG. 1, except that each banana coil 1210, 1214, 1218, 1222 is provided with a supplementary rectangular coils 1212, 1216, 1220, 1224 situated on the inside arc of the banana, with the current direction of the respective coils of the quadrant being opposite. The coil arrangement of FIG. 12 may be provided as a main field generating means in an embodiment of the present invention.

A configuration for the placement of magnetic coils suitable for a magnetic resonance imaging assembly such as has been described provides numerous advantages arising from the design: high levels of patient access are afforded by way of the open design; since the overall magnetic field is generated perpendicular to the configuration in direction 110, parallel to the midplane XY. The magnetic forces of attraction between opposing coils either side of the imaging volume are reduced allowing the construction of the supports between the coil groups to be less substantial than is known for conventional open- or C-magnets; patients may be aligned head-to-toe along the magnetic field of at any angle thereto; the use of smaller magnets with a concomitant reduction in the amount of conductor wire can achieve useful savings in manufacturing costs.

The above arrangements have been found suitable for incorporation into particle radiation therapy equipment.

The present invention provides an application of the magnetic coils arrangements described above to provide improved particle radiation therapy equipment. According to the present invention, a charged particle beam source 101 (FIG. 1) is arranged to direct a charged particle beam 102 in a predetermined direction to a region of application. Furthermore, magnetic field generation means are provided for generating a magnetic field in the region of application at the same time that the charged particle beam is applied, wherein the magnetic field generation means is arranged to provide access to the region of application for the charged particle beam, and to provide a homogeneous magnetic field in the region of application of the charged particle beam, said magnetic field being directed substantially in the predetermined direction.

Preferably, the magnetic field generation means comprises one of the coil arrangements discussed above. In this case, the magnetic field generation means may comprise magnetic coils, each comprising windings of electrically conductive material; wherein the magnetic coils are arranged symmetrically about a midplane (XY) and a plane of reflection (YZ), the plane of reflection being perpendicular to the midplane, such that the coils have a plane of symmetry with respect to another plane (XZ), which is perpendicular to both the midplane and the plane of reflection. Each of the coils is preferably being wound around an axis which is perpendicular to the midplane. In operation, current flow is preferably symmetrical about the plane of reflection and anti-symmetrical about the midplane, to produce a resultant field B at the centre of the system which is perpendicular to the plane of reflection, and is directed substantially in the predetermined direction.

In certain embodiments, the magnet coils are arranged in a group of four sets of coils, and the sets of magnetic coil are arranged symmetrically as defined above.

The magnetic field generation means is preferably adapted for use in a magnetic resonance imaging system, such that magnetic resonance imaging of the region of application of the charged particle beam may be performed at the same time as the application of the charged particle beam.

The particle radiation therapy equipment preferably also comprises a cryostat unit and a gradient magnet assembly, wherein the said magnetic field generation means is situated within the cryostat to provide an operating temperature at which superconductivity is possible, and wherein the gradient magnet assembly is operable to provide magnetic fields across predetermined planes so as to enable magnetic resonance imaging.

The present invention also provides a method for performing particle radiation therapy on a patient at the same time as magnetic resonance imaging is performed on the patient. A charged particle beam is applied to a region of application of the patient in a predetermined direction. A homogeneous magnetic field is generated in the region of application of the charged particle beam, said magnetic field being directed substantially in the predetermined direction.

Preferably, the homogeneous magnetic field is generated by magnetic coils, each comprising windings of electrically conductive material; wherein the magnetic coils are arranged symmetrically about a midplane (XY) and a plane of reflection (YZ), the plane of reflection being perpendicular to the midplane, such that the coils have a plane of symmetry with respect to another plane (XZ), which is perpendicular to both the midplane and the plane of reflection, each of the coils being wound around an axis which is perpendicular to the midplane, and wherein the windings are configured such that, in operation, current flow is symmetrical about the plane of reflection and anti-symmetrical about the midplane, to produce a resultant field at the centre of the system which is perpendicular to the plane of reflection, and is directed substantially in the predetermined direction.

In certain embodiments, the magnet coils are arranged in a group of four sets of coils, and the sets of magnetic coil are arranged symmetrically as defined above.

The method may further comprise cooling the magnet coils to a temperature at which superconductivity is possible and flowing current in the magnetic coils such that the direction of current flow is symmetrical about the plane of reflection and anti-symmetrical about the midplane.

While the present invention has been described with reference to a limited number of specific embodiments, by way of examples only, those skilled in the art will appreciate that numerous modifications and variations of the present invention may be derived within the scope of the appended claims.

The invention claimed is:

1. Particle radiation therapy equipment arranged to apply a charged particle beam, in a predetermined direction, to a region of application, said radiation therapy equipment comprising:
    a charged particle beam source arranged to direct a charged particle beam in the predetermined direction; and
    magnetic field generation means for generating a magnetic field in an imaging volume which includes the region of application, at the same time that the charged particle beam is applied; wherein,
    the magnetic field generation means is arranged to provide access to the region of application, and to provide a homogeneous magnetic field in the region of application, said magnetic field being directed substantially in the predetermined direction;
    the magnetic field generation means comprises magnetic coils, each comprising windings of electrically conductive material;
    the magnetic coils are arranged symmetrically about a midplane (XY) and about a plane of reflection (YZ) that is perpendicular to the midplane (XY), such that the magnetic coils have a further plane of symmetry (XZ), which is perpendicular to both the midplane (XY) and the plane of reflection (YZ);
    each of the coils is wound around an axis that is perpendicular to the midplane (XY); and
    the windings are configured such that, in operation, current flow is symmetrical about the plane of reflection (YZ) and anti-symmetrical about the midplane (XY), to produce a resultant field at the center of the magnetic field generation means which is perpendicular to the plane of reflection (YZ), parallel to the midplane (XY), and directed substantially in the predetermined direction.

2. The particle radiation therapy equipment according to claim 1, wherein:
    the magnetic coils are arranged in a group of four sets of coils; and
    the sets of coils are arranged symmetrically about the midplane (XY) and the plane of reflection (YZ), such that the magnetic coils are symmetrical about the further plane of symmetry (XZ).

3. The particle radiation therapy equipment according to claim 1, where the magnetic coils comprise D coils.

4. The particle radiation therapy equipment according to claim 1, wherein the magnetic coils comprise banana coils.

5. The particle radiation therapy equipment according to claim 1, wherein the magnetic coils comprise sub-coils.

6. The particle radiation therapy equipment according to claim 5, wherein the sub-coils are provided in one of a nested arrangement and an overlapping arrangement.

7. The particle radiation therapy equipment according claim 1, wherein the coils are non-planar.

8. The particle radiation therapy equipment according to claim 1, wherein the magnetic field generation means is adapted for use in a magnetic resonance imaging system.

9. The particle radiation therapy equipment according to claim 1, further comprising a cryostat unit and a gradient magnet assembly, wherein:
    the magnetic field generation means is situated within the cryostat that provides an operating temperature at which superconductivity is possible; and
    the gradient magnet assembly is operable to provide magnetic fields across predetermined planes, thereby enabling magnetic resonance imaging.

* * * * *